US00PP24637P3

(12) United States Plant Patent
Brazelton et al.

(10) Patent No.: US PP24,637 P3
(45) Date of Patent: Jul. 15, 2014

(54) BLUEBERRY PLANT NAMED 'ZF05-196'

(50) Latin Name: ***Vaccinium corymbosum* hybrid**
Varietal Denomination: ZF05-196

(75) Inventors: David M. Brazelton, Walterville, OR (US); Adam L. Wagner, Eugene, OR (US)

(73) Assignee: Fall Creek Farm and Nursery, Inc., Lowell, OR (US)

( * ) Notice: Subject to any disclaimer, the term of this patent is extended or adjusted under 35 U.S.C. 154(b) by 150 days.

(21) Appl. No.: 13/385,888

(22) Filed: Mar. 12, 2012

(65) Prior Publication Data

US 2013/0239259 P1 Sep. 12, 2013

(51) Int. Cl.
*A01H 5/00* (2006.01)

(52) U.S. Cl.
USPC ..... Plt./157

(58) Field of Classification Search
CPC ..... A01H 5/08
USPC ..... Plt./157
See application file for complete search history.

*Primary Examiner* — June Hwu
(74) *Attorney, Agent, or Firm* — Davis Wright Tremaine LLP; Dale C. Hunt; Wenhua Yu

(57) ABSTRACT

The new blueberry plant variety 'ZF05-196' is provided. 'ZF05-196' is a nursery variety intended for the landscape and home garden markets. The variety produces high yields of medium sized fruit with nice flavor and firmness. 'ZF05-196' is a mid-season variety. The variety is very vigorous with an upright stature and attractive, long fruit clusters.

3 Drawing Sheets

Latin name of the family, genus, and species: Family—Ericaceae. Genus—*Vaccinium*. *Species—corymbosum* hybrid.

Variety denomination: The new blueberry plant claimed is of the variety denominated 'ZF05-196.'

CROSS REFERENCE TO RELATED APPLICATIONS

None.

STATEMENT REGARDING FEDERALLY-SPONSORED RESEARCH AND DEVELOPMENT

None.

BACKGROUND OF THE INVENTION

The present invention relates to the discovery of a new and distinct cultivar of northern highbush blueberry known as a *Vaccinium corymbosum* hybrid referred to as 'ZF05-196', as herein described and illustrated.

The new blueberry plant variety 'ZF05-196' was selected in Lowell, Oreg. in 2005. 'ZF05-196' is a nursery variety intended for the landscape and home garden markets. The variety produces high yields of medium sized fruit with nice flavor and firmness. 'ZF05-196' is is a mid-season variety, ripening after Draper (U.S. Plant Pat. No. 15,103) and before Liberty (U.S. Plant Pat. No. 15,146). The variety is very vigorous with an upright stature and attractive, long fruit clusters.

Pedigree and History: The new blueberry plant originated from a cross of 'Duke' (female parent, unpatented) by 'Legacy' (pollen parent, unpatented). The new blueberry plant variety 'ZF05-196' has been planted in replicated trials since 2007.

The new variety can be compared to female parent 'Duke' in that 'ZF05-196' is more upright, has longer fruit clusters, a higher yield and ripens about 2 to 3 weeks later.

The new variety can be compared to commercial variety 'Liberty' in that 'ZF05-196' has a higher yield, larger berries and ripens about one week earlier.

The new blueberry plant variety 'ZF05-196' has maintained its distinguishing characteristics throughout successive asexual propagations. The variety has been repeatedly asexually reproduced through softwood cuttings in Lowell, Oreg., and the clones are phenotypically identical to the original plant.

SUMMARY OF THE INVENTION

The new blueberry plant variety 'ZF05-196' has not been observed under all possible environmental conditions. The phenotype may vary somewhat with variations in environment and cultural practices such as temperature and light intensity without, however, any variance in genotype.

The following traits have been repeatedly observed in Lowell, Oreg., and are determined to be the unique characteristics of the new blueberry plant variety 'ZF05-196':

1. Vigorous plant with upright stature.
2. Long, loose fruit clusters.
3. High yields.

BRIEF DESCRIPTION OF THE DRAWINGS

The accompanying photographic illustration shows typical specimens in full color of the foliage and fruit of the new variety 'ZF05-196'. The colors are a nearly true as is reasonably possible in a color representation of this type.

BOTANICAL DESCRIPTION

Figure 1:
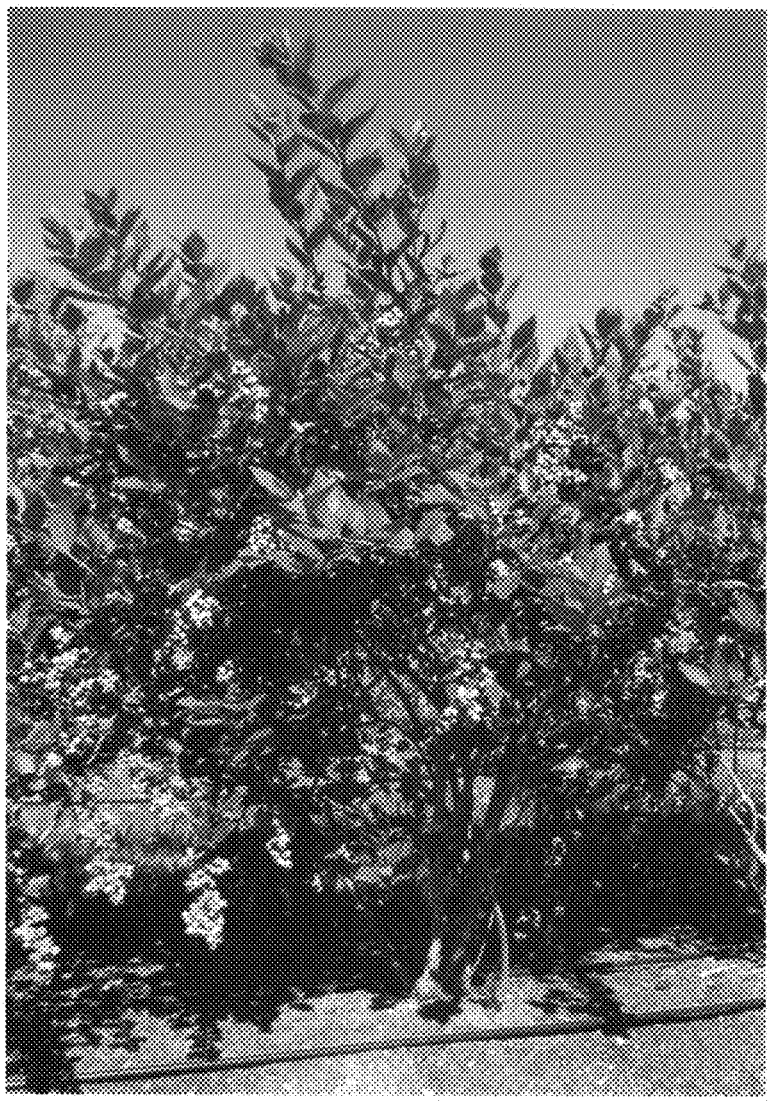
FIG. 1 is a photograph of the new variety 'ZF05-196'.
Figure 2:
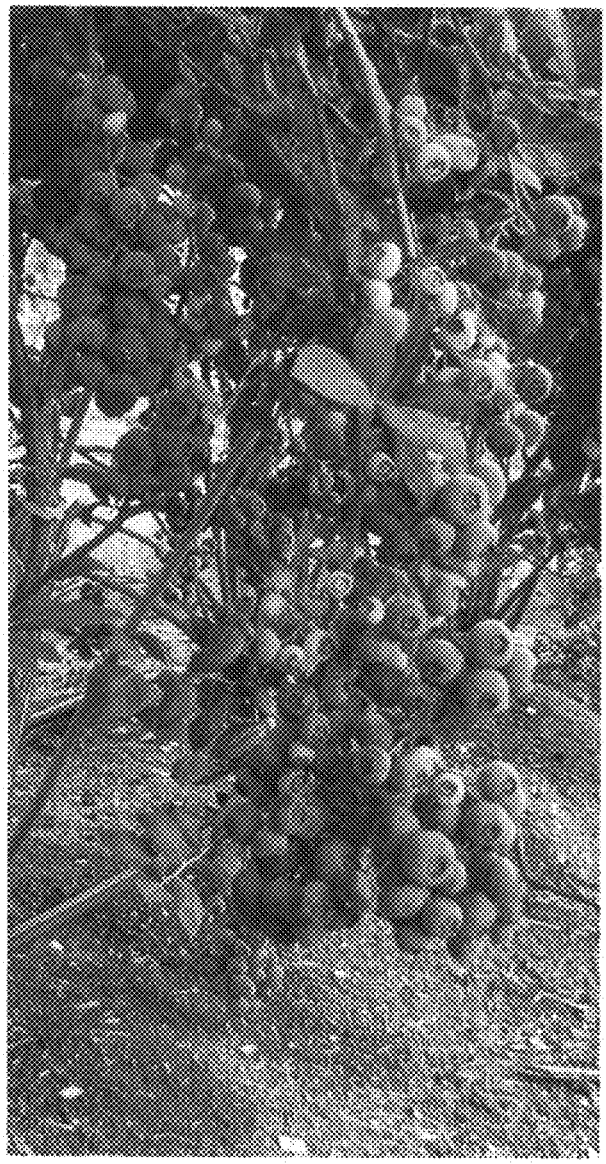
FIG. 2 is a photograph of the fruit of the new variety 'ZF05-196'.
Figure 3:
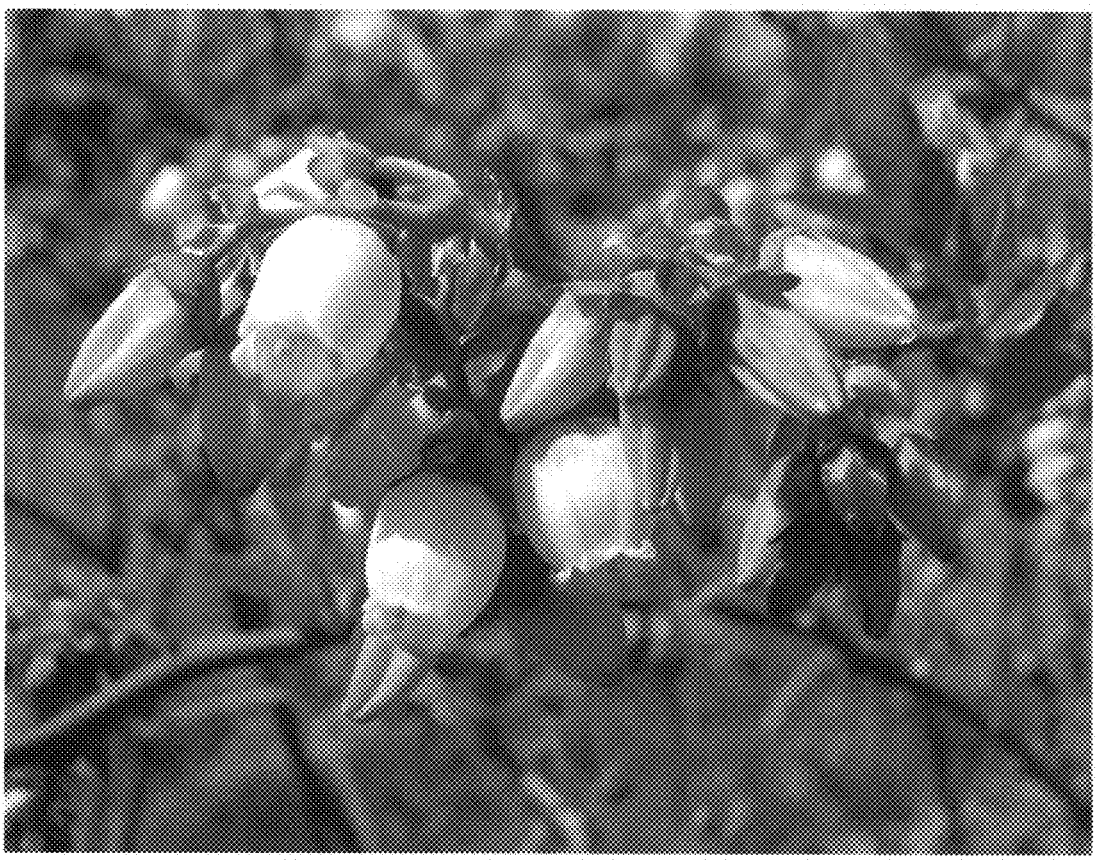
FIG. 3 is a photograph of the flowers of the new variety 'ZF05-196'.

The following detailed description sets forth the distinctive characteristics of 'ZF05-196'. The data which defines these characteristics was collected from asexual reproductions of the original selection. Dimensions, sizes, colors, and other characteristics are approximations and averages set forth as accurately as possible. The plant history was taken on plants approximately three years of age, and the descriptions relate to plants grown in the field in Lowell, Oreg. Color designations are from "The Pantone Book of Color" (by Leatrice Eiseman and Lawrence Herbert, Harry N. Abrams, Inc., Publishers, New York, 1990). Where the Pantone color designations differ from the colors in the photographs, the Pantone colors are accurate.

Classification:

*a. Family.*—Ericaceae.

*b. Genus.*—*Vaccinium.*

*c. Species.*—*corymbosum* hybrid.

*d. Common name.*—Northern Highbush Blueberry.

Parentage:

*Female parent.*—Duke (unpatented).

*Male parent.*—Legacy (unpatented).

Market class: 'ZF05-196' is a nursery variety intended for the landscape and home garden markets.

PLANT

Plant size:

*a. Height of plant.*—Average of 49 inches on 4 year old plants.

*b. Canopy diameter.*—Average of 44 inches on 4 year old plants.

Growth habit: Upright.

Plant vigor: Vigorous.

Twigginess: Not twiggy.

Suckering: Low.

Evergreenness: Deciduous.

Chilling requirement: Approximately 700-1000 hours.

Cold hardiness: Approximately USDA zones 4-8.

Productivity in Lowell, Oreg.:

*a. 4 year old plants.*—Produced an average of 6.85 lbs per plant, compared to Liberty plants of the same age which produced an average of 7.46 lbs per plant.

*b. 5 year old plants.*—Produced an average of 14 lbs per plant, compared to Liberty plants of the same age, which produced an average of 8.9 lbs per plant.

Propagation: Easy to propagate from softwood cuttings.

Disease and pest resistance/susceptibility:

*a. Root rot* (*Phytophthora cinnamomi*).—Does not appear to be overly susceptible.

*b. Stem blight* (*Botryosphaeria spp*).—Undetermined.

*c. Phomopsis twig blight* (*Phomopsis vaccinii*).—Does not appear to be overly susceptible.

*d. Botryosphaeria stem canker* (*Botryosphaeria corticis*).—Undetermined.

*e. Bacterial cane canker* (*Pseudomonas syringae*).—Does not appear to be overly susceptible.

*f. Botrytis blight* (*Botrytis cinerea*).—Does not appear to be overly susceptible.

*g. Leaf spot* (*Septoria spp.*).—Does not appear to be overly susceptible.

*h. Leaf rust* (*Naohidemyces vaccinii*).—Does not appear to be overly susceptible.

*i. Bud mites* (*Acalatus vaccinii*).—Undetermined.

Disease survival: Good.

WOOD

Texture:

*a. Surface texture new wood.*—Smooth.

*b. Surface texture 1 year wood.*—Smooth.

*c. Surface texture 3 year wood.*—Smooth turning rough.

Color:

*a. Color new wood.*—Pantone color Green Banana 14-0434.

*b. Color rough bark 1 year.*—Pantone colors: Catchup 18-1449, Hay 12-0418, and Green Banana 14-0434.

*c. Color rough bark 3 year.*—Pantone colors: Desert Dust 13-1018, Tobacco Brown 17-1327, and Gray Sand 13-1010.

LEAVES

Internode length: Average of 16.5 mm.

Dimensions:

*a. Leaf length.*—Average 72.5 mm.

*b. Leaf width.*—Average 41.14 mm.

Leaf shape: Elliptical with acute apex and rounded base.

Leaf margin: Entire.

Color:

*a. Leaf color upper leaf surface.*—Pantone color Chive 19-0323.

*b. Leaf color lower leaf surface.*—Pantone color Mistletoe 16-0220.

Fall leaf color: Pantone Crimson 19-1762.

Pubescence:

*a. Pubescence upper leaf surface.*—Absent.

*b. Pubescence lower leaf surface.*—Absent.

*c. Pubescence leaf margins.*—Absent.

Petiole:

*a. Petiole length.*—Average of 4.78 mm.

*b. Petiole color.*—Pantone color Hay 12-0418 and Catchup 18-1449.

*c. Petiole surface texture.*—Smooth.

Leafing vs flowering: In Lowell, Oreg. flower bud break occurs prior to vegetative bud break. Flowers persist during initial vegetative growth period.

FLOWERS

Flower arrangement: Flower clusters arranged alternately along branch.

Immature flower color: Pantone colors Mauveglow 16-1617 and Snow White 11-0602.

Fragrance: Faint, Sweet.

Flower shape: Urceolate to cylindrical.

Flower length: Average of 10.4 mm.

Pedicel:

*a. Pedicel length flower.*—Average of 4.55 mm.

*b. Pedicel color.*—Pantone color Green Olive 17-0535; Pantone color Wild Rose 16-1715.

Peduncle:

*a. Peduncle length flower.*—Average of 15.76 mm.

*b. Peduncle color.*—Pantone colors Green Banana 14-0434 and Red Earth 18-1444.

Pollen:

*a. Pollen staining.*—Approximately 95% viable, staining with 2% acetocarmine dye.

*b. Pollen abundance.*—Medium.

*c. Pollen color.*—Pantone color Cornsilk 13-0932.

Corolla:

*a. Corolla length*.—Average of 8.25 mm.

*b. Corolla diameter*.—Average of 7.4 mm.

*c. Corolla aperture*.—Average of 4.29 mm.

*d. Corolla color*.—Pantone color Snow White 11-0602.

*e. Corolla texture*.—Smooth.

Style length: Average of 7.52 mm.

Calyx:

*a. Calyx diameter*.—Average of 6.52 mm.

*b. Calyx surface*.—Smooth.

*c. Calyx color*.—Pantone colors Spinach Green 16-0439, lobes Green Oasis 15-0538; Lilas 16-1708.

Pistil color: Pantone color Green Olive 17-0535.

Flowering cluster: Loose.

Flowering period: Begins flowering in mid-April, reaching 50% bloom in the first week of May and continues flowering through the end of May.

Number flowers: Average of 7 to 8.

Stigma location: Average 0.1 mm above or even with the lip of corolla.

Anther:

*a. Anther length*.—Average of 4.11 mm.

*b. Anther color*.—Pantone color Autumn Leaf 17-1347.

Self-compatibility: Low. Approximately 18% of self-pollinated flowers reach maturity (this pollination trial was completed on field plants and may not accurately represent the self-compatibility of this variety. Trials were repeated in 2012).

Updated self-compatibility: Low. Out of 75 flowers pollinated in the greenhouse in 2012, only 25 (33%) formed fruit. Out of 46 flowers pollinated in the field, only 7 (15%) formed fruit.

Average inflorescence size: 30.66 mm.

BERRIES

Mean harvest date: August 4.

Mean date last pick: August 25.

Quantity berries per cluster: Average of 7 to 8 berries per cluster.

Calyx:

*a. Calyx aperture*.—Average of 5.06 mm.

*b. Calyx lobes*.—5 moderately distinct lobes.

*c. Calyx depth*.—Average of 1.68 mm.

Berry cluster: Loose.

Berry pedicel:

*a. Length*.—Average of 10.19 mm.

*b. Surface texture*.—Smooth.

Berry peduncle:

*a. Length*.—Average of 29.93 mm.

*b. Surface texture*.—Smooth.

Berry detachment: Easy.

Berry weight: Average of 2.4 g per berry, compared to Liberty which has an average berry size of 2.2 g.

Berry height: Average of 13.39 mm.

Berry width: Average of 18.42 mm.

Berry shape: Round to oblate.

Berry skin color:

*a. Immature berry color*.—Pantone color Celery Green 13-0532.

*b. Berry skin color on plant*.—Pantone color Gray Dawn 14-4106.

*c. Berry skin color after harvest*.—Pantone color Gray Dawn 14-4106.

*d. Berry skin color after polishing*.—Pantone color India Ink 19-4019.

Berry wax: Medium wax, moderately persistent.

Berry flesh color: Pantone color Water Lily 11-0304.

Pedicel scar: Small and dry.

Berry firmness: Firm.

Berry flavor: Sweet, fruity.

Berry texture: Smooth and firm.

SEEDS

Seed color: Pantone color Tortoise Shell 19-1241.

Seed length: Average of 1.64 mm.

Seed width: Average of 1.09 mm.

Seed weight: Average of 0.3 mg.

Quantity seeds per berry: Average of 36 seeds per berry.

DISTINGUISHING FEATURES FROM MALE PARENT 'LEGACY'

TABLE 1

| Name of paternal parent | Characteristic(s) in which the candidate variety differs from the paternal parent | Describe the expression of the characteristic for the paternal parent | Describe the expression of the characteristic for 'ZF05-196' |
|---|---|---|---|
| Legacy | Average time of 50% ripe fruit in Lowell, OR | July 27 | July 16 |
| Legacy | Leaf width | Medium | Very broad |

The invention claimed is:

1. A new and distinct variety of blueberry plant named 'ZF05-196', substantially as illustrated and described herein.

* * * * *